(12) United States Patent
Buthier

(10) Patent No.: US 7,028,917 B2
(45) Date of Patent: Apr. 18, 2006

(54) AIR FRESHENING DEVICE

(75) Inventor: Bruno Buthier, Lucé (FR)

(73) Assignee: Reckitt Benckiser (UK) Limited, Slough (GB)

( * ) Notice: Subject to any disclaimer, the term of this patent is extended or adjusted under 35 U.S.C. 154(b) by 0 days.

(21) Appl. No.: 10/466,133

(22) PCT Filed: Jan. 15, 2002

(86) PCT No.: PCT/GB02/00142

§ 371 (c)(1),
(2), (4) Date: Dec. 16, 2003

(87) PCT Pub. No.: WO02/055116

PCT Pub. Date: Jul. 18, 2002

(65) Prior Publication Data

US 2004/0135000 A1    Jul. 15, 2004

(30) Foreign Application Priority Data

Jan. 15, 2001  (GB) ................................. 0101010
Nov. 7, 2001  (GB) ................................. 0126751

(51) Int. Cl.
   *A24F 25/00*   (2006.01)
   *A61L 9/04*    (2006.01)
(52) U.S. Cl. .......................................... 239/60; 239/34
(58) Field of Classification Search ................ 239/60, 239/34, 36, 47, 53, 326; 425/127; 249/58, 249/117, 139
See application file for complete search history.

(56) References Cited

U.S. PATENT DOCUMENTS

| 2,561,592 | A | * | 7/1951  | Palmer ........................ 261/24 |
| 2,740,662 | A | * | 4/1956  | Scott ........................... 239/55 |
| 3,031,146 | A | * | 4/1962  | Albamonte ................... 239/57 |
| 3,910,495 | A |   | 10/1975 | Cummings et al. ........... 239/58 |
| 4,840,770 | A | * | 6/1989  | Walz et al. ................... 422/49 |
| 5,060,858 | A |   | 10/1991 | Santini ......................... 239/60 |
| 5,324,490 | A |   | 6/1994  | Van Vlahakis et al. ..... 422/305 |
| 5,419,879 | A |   | 5/1995  | Vlahakis et al. ............ 422/305 |
| 6,039,266 | A |   | 3/2000  | Santini ......................... 239/60 |

FOREIGN PATENT DOCUMENTS

| GB | 1473625   | 5/1977  |
| GB | 2289410 A | 11/1995 |
| GB | 2350300 A | 11/2000 |

* cited by examiner

*Primary Examiner*—David A. Scherbel
*Assistant Examiner*—Darren Gorman
(74) *Attorney, Agent, or Firm*—Norris McLaughlin & Marcus PA

(57) ABSTRACT

The invention relates to improvements in or relating to containers and in particular to an air freshening or purifying device utilizing a gel fragrance or other composition suitable for use in a vehicle. The air freshening or purifying device comprises a gel holder having at least one recess for receiving a gel, wherein a plurality of prongs project from a base of the recess, the prongs being inclined in at least two different directions to an axis perpendicular to the recess base.

16 Claims, 4 Drawing Sheets

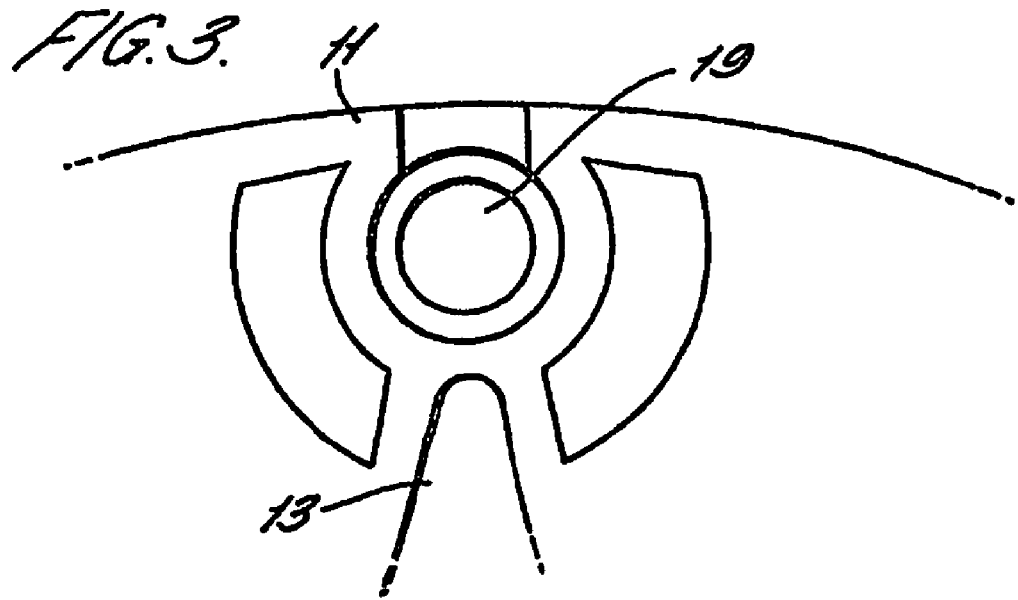
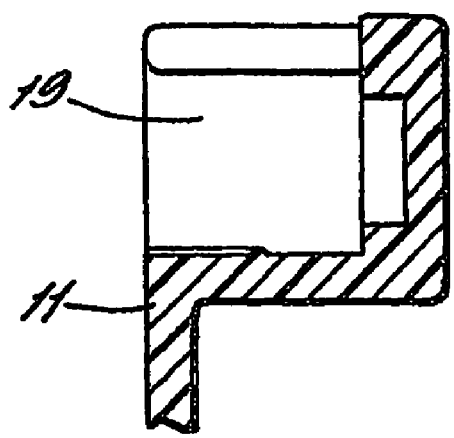
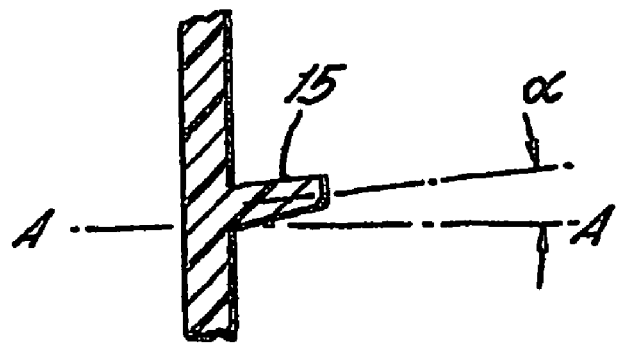

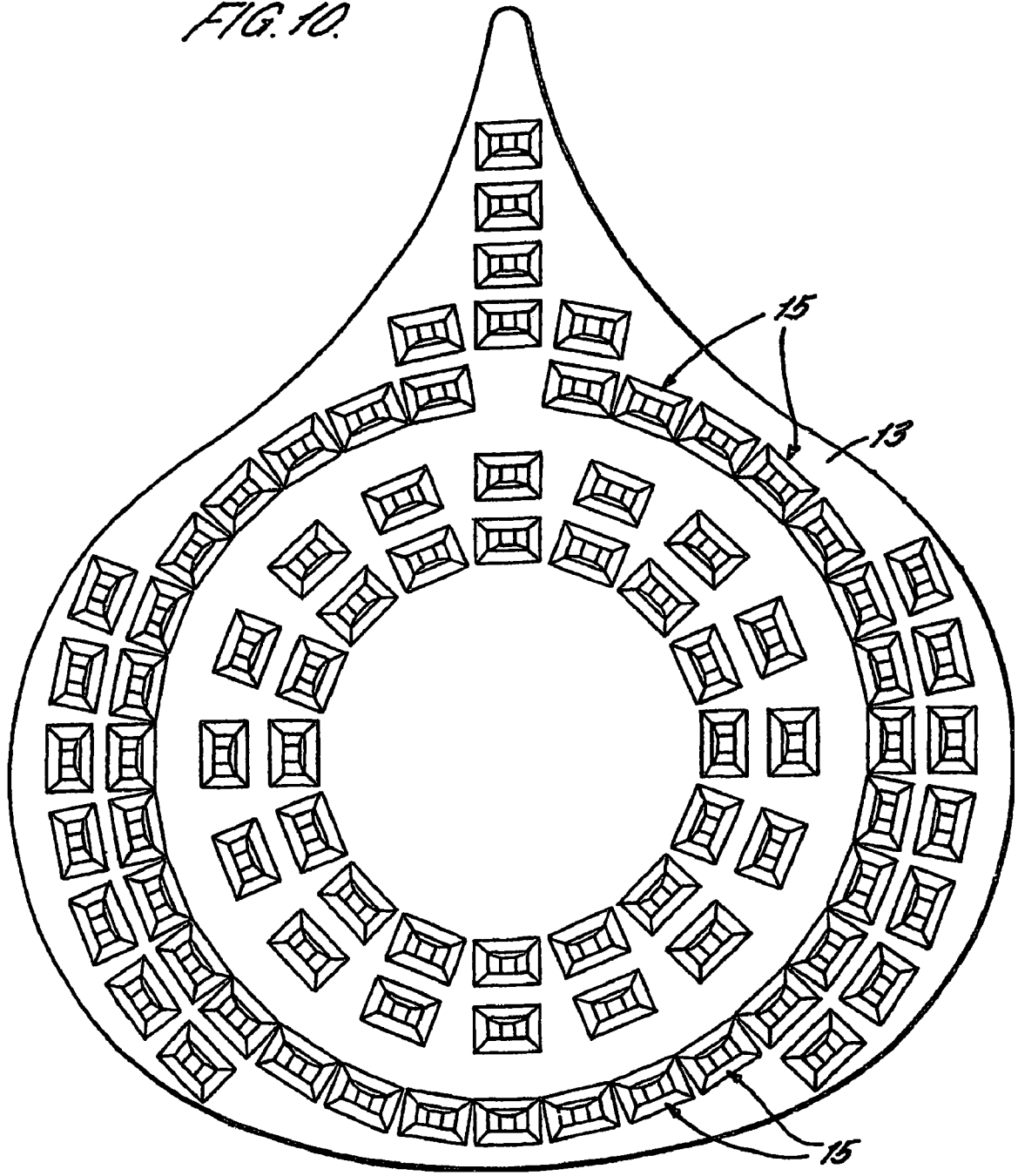

AIR FRESHENING DEVICE

BACKGROUND OF THE INVENTION

The invention relates to improvements in or relating to containers and in particular to a device for an air freshener or purifier utilizing a gel fragrance or other composition suitable for use in a vehicle.

Many devices are known which can be used in cars or other vehicles as air fresheners. In this specification the term "fragrance" may be a simple perfume, that also includes a deodorant which itself may or may not be perfumed. One form consists of a plastic container adhered to the dashboard or another part of the vehicle containing a fragrance in solid form. The fragrance evaporates over a period of time and is released through slots in the container. Disadvantageously such devices are usually positioned in a place where they could be knocked off unless the adhesive is particularly strong. If the adhesive is too strong, then this marks the dashboard when the air freshener is replaced.

Another common form of air freshening device comprises a substrate of card, wood or the like which is impregnated with a fragrance, which is hung from the rear view mirror. Some of these devices do not last very long and others are very unattractive, in appearance.

Recently there has been a marked increase in the use of fragrances in gel form. The devices for dispensing such fragrances are commonly provided by plastic packaging elements in which the diffusion of the fragrance takes place through the semi-permeable walls of a polymeric material.

U.S. Pat. No. 5,780,527 describes such angel which can be used as a fragrancing component in such an air freshening device. This gel is particularly advantageous in that it can be used in attractively shaped open containers without the need for sealing.

A gel fragrance is used in one air freshening device, which is currently on the market for home use, which comprises an attractive glass disk having grooves in one surface thereof containing the gel. As the fragrance is dissipated over time, the gel shrinks and is no longer supported by all of the groove walls. To prevent the shrinking gel from falling out of the container, a number of small grooves are used which are fairly narrow. However, in a smaller version of the device a series of small grooves may not be possible and other means must be found to ensure that the gel does not leak out of the device.

SUMMARY OF THE INVENTION

It is therefore an object of the present invention to provide an air freshening or purifying device utilizing a gel fragrance or other gel composition which has a convenient construction suitable for use in a vehicle, which has an attractive appearance and which can provide long lasting air freshening, or other, action in which a larger quantity of gel may be used than those known in the art.

According to the invention there is produced a device for an air freshener or purifier comprising a gel holder having at least one recess with a base for receiving a gel composition, wherein a plurality of prongs project from the base of the recess, the prongs each having at least three, preferably four sides, said sides being inclined to an axis substantially perpendicular to the recess base except for one side which is substantially perpendicular to the recess base.

Preferably the prongs are arranged such that their substantially perpendicular sides are located further away from the centre of the recess than the inclined sides.

Preferably the angle of inclination of the inclined sides is in the range of 2 to 4° to the perpendicular axis.

The angle of inclination of the inclined sides is preferably in the range of 2 to 4° to the perpendicular axis.

The present invention also provides an air freshening or purifying device comprising a gel holder having at least one recess for receiving a gel composition, wherein a plurality of prongs project from the base of the recess, at least a majority of said prongs being inclined relative to an axis perpendicular to the recess base.

Advantageously the gel is held in place simply by the prongs. When it shrinks due to fragrance being lost (it may be up to 80% fragrance), it retains its shape.

Preferably the prongs are inclined in at least two and more preferably four different directions.

A majority of the prongs may be provided in a plurality of rows.

A majority of the prongs may be provided in a plurality of groups.

Preferably a majority of the prongs are arranged in rows, and the angle of inclination of the prongs in at least one row being towards the east, in at least another row to the west, in at least another row to the north and in at least another row to the south.

Preferably a majority of the prongs are arranged in the configuration of a cross having four arms with groups of prongs providing said arms, the angle of inclination of each group being different, namely towards the east, west, north and south respectively.

A majority of the prongs are preferably provided in a plurality of concentric circular rows and/or arcs.

The air freshening device may further comprise hanging means for suspending the device.

The hanging means are preferably removably or, permanently attached, for example, to the gel holder.

Preferably the gel holder is provided with a plurality of gel receiving recesses.

Preferably the gel holder is of a transparent material.

The gel holder is preferably of a plastics material.

The number of prongs preferably lies in the range of 10 to 100.

The length of the prongs preferably lies in the range of 1 mm to 10 mm.

The prongs are either straight, tapered or hooked.

Preferably the angle of inclination of the prongs lies in the range of 4° to 50°, and more preferably the angle of inclination is 8°.

The device preferably incorporates a gel composition, which may be a fragrance or air purifying composition or an insecticide.

The invention also provides a method of manufacturing such a device comprising the steps of forming the gel holder, filling the recess with the gel composition and allowing it to set.

The prongs of the gel holder are preferably formed at an inclined angle or alternatively they are formed substantially perpendicular to the recess base and then deformed to an inclined angle.

A preferred embodiment of the present invention will now be described, by way of example only, with reference to the accompanying drawings, in which:

BRIEF DESCRIPTION OF THE SEVERAL VIEW OF THE DRAWING

FIG. 3 is an enlarged front elevation of the socket for the ball of the hanging means;

FIG. 4 is an enlarged cross-sectional side elevation of the socket of FIG. 3; and FIG. 5 is an enlarged cross-sectional side elevation of one of the prongs of FIG. 2;

FIG. 10 is front elevation of the gel holder having an alternative configuration of prongs.

DETAILED DESCRIPTION OF THE INVENTION

Figure 1:
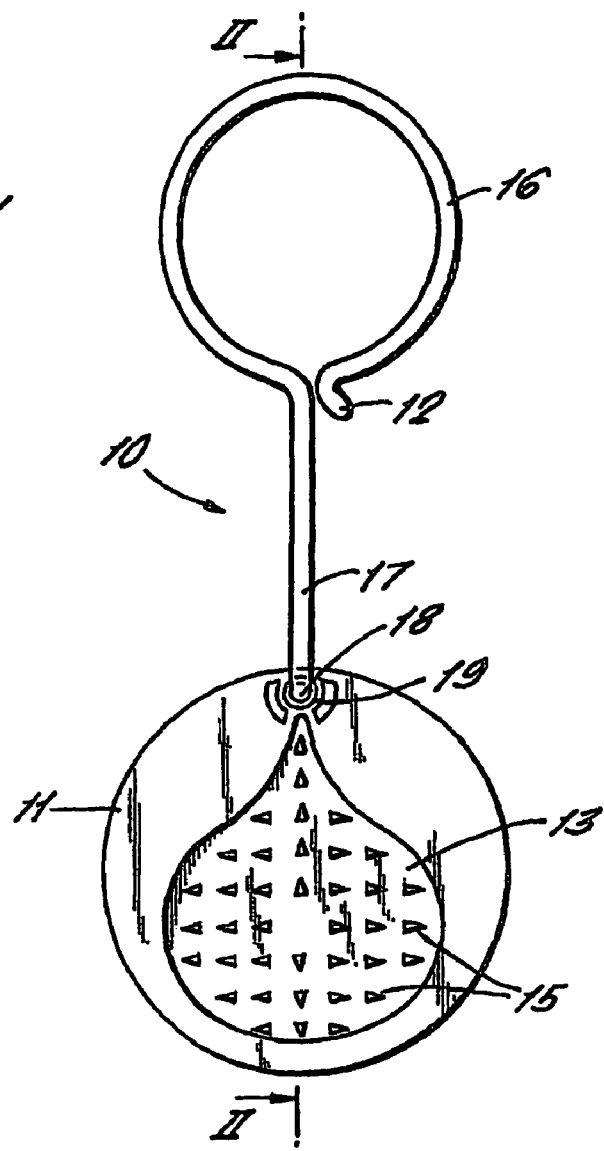
FIG. 1 is a front elevation of an air freshening device according to the present invention.

Referring to FIG. 1 there is shown an air freshening device 10 which comprises a gel holder 11 and hanging means 12.

The gel holder 11 illustrated is in the shape of a disk, but can be of any desired shape. The gel holder 11 has a recess 13 for receiving a gel composition, preferably of the type described in U.S. Pat. No. 5,780,527. The recess 13 illustrated in FIG. 1 is a tear drop, which is an attractive shape, but again this can be of any desired shape. When filled with the gel, which is preferably strongly coloured, the shape of the recess 13 is highlighted.

Figure 2:
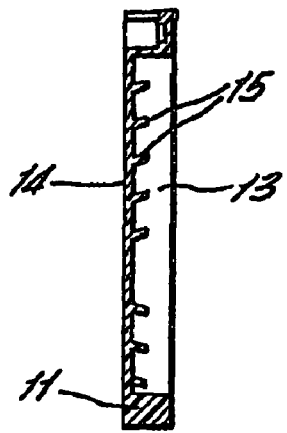
FIG. 2 is a cross sectional side elevation shown on the line II—II of the gel holder of the air freshening device of FIG. 1.
Figure 7:
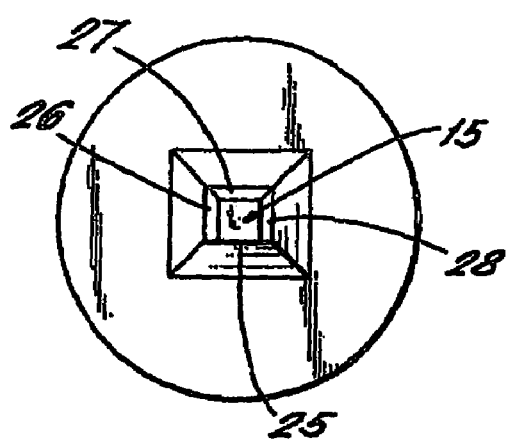
FIGS. 6 to 9 are respectively pictorial views, plan elevations side and end elevations of an alternative configuration of prongs.
Figure 6:
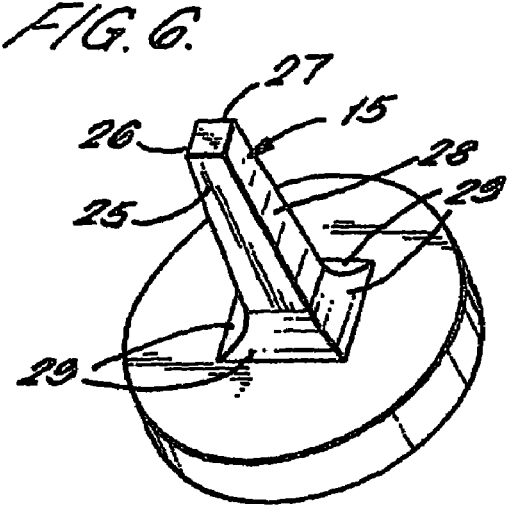
Figure 9:
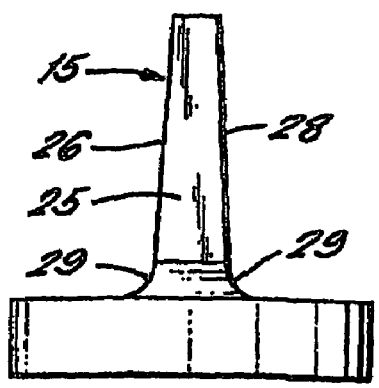
Figure 8:
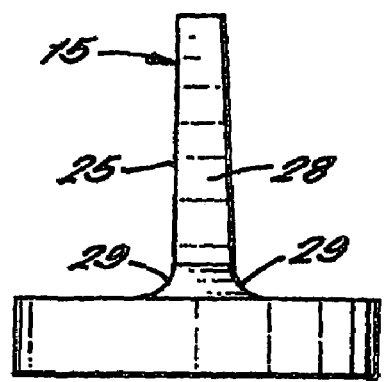

Projecting from the base 14 of the recess 13 is a plurality of small prongs 15 (see FIGS. 2 and 5). These prongs 15 can be spiked, hooked, tapered or of other similar configurations. The prongs 15 may be perpendicular to the recess base 14 or a majority or all of them may alternatively be inclined with respect to an axis AA which is substantially perpendicular to the recess base 14.

In one embodiment of the invention the prongs may be provided in a plurality of horizontal rows, with the upper rows inclined slightly towards the hanging means 12 (i.e. in a northerly direction) and the lower rows inclined oppositely towards the bottom of the holder 11 (i.e. towards the south). Thus the prongs 15 are inclined in two different directions with respect to axis AA. In the embodiment illustrated, the pattern is more complicated, and one central vertical row is angled to the north, one central row is inclined to the south and the rows at either side of the central row are angled to the east and west respectively.

In a further embodiment of the invention the rows of prongs 15 are provided in the pattern of a cross, with four groups of rows of prongs providing the arms. Each group of prongs is inclined differently, towards the east, west, north and south respectively, i.e. four different directions.

In the previously described embodiments, the prongs are provided in straight rows having an essentially square configuration. In a preferred embodiment, the pattern of distribution is circular rather than square as shown in FIG. 10. The circular distribution gives better gel retention characteristics, because the shrinkage is homotetic to the initial conformation of the gel.

The prongs 15 are preferably at least four sided, more preferably rectangular in cross-section, and taper from the base of the prong 15 to the tip. Most preferred is the configuration of the prongs 15 shown in FIGS. 6 to 9 in which the prongs are rectangular in cross-section but have one perpendicular side 25 and the remaining three sides 26, 27, 28 are inclined. The angle of inclination is preferably in the order of 2° to 4° and most preferably 3° to the perpendicular. When this configuration of prongs 15 is used, the prongs 15 have their perpendicular sides 25 substantially directed away from the centre of the recess 13, i.e. at the furthest point from the centre of the recess than the other sides, and thus oppose the tension of the gel.

The number of prongs 15 preferably lies in the range of 10 to 100 and the length of the prongs 15 is preferably in the range of 1 mm to 10 mm and most preferably 4 mm.

A preferred size of the tip of the prongs 15 is in the range of 0.4 mm to 1 mm and more preferably 0.6 mm². The prongs 15 preferably have a radius 29 where they meet the recess base 14 and this radius may typically be in the region of 0.3 mm to 0.8 mm and preferably 0.5 mm.

The angle of inclination α of the inclined prongs 15 shown in FIG. 5 preferably lies in the range of 4° to 50° and is most preferably 8°.

The actual number of prongs 15, their positioning, their length, their angle of inclination α and the number of different angles of inclination used will at least partly depend on the size and shape of the recess 13. The angle of inclination α is also partly dependent on the process used to form the gel holder 11.

The hanging means 12 can be of any suitable shape which would allow the air freshening device 10 to be removably attached to a fixed element in the car, e.g. the stem of the rear view mirror. Thus the hanging means 12 has a hook 16 at one end and a stem 17. The stem 17 is either permanently or removably attached to the gel holder 11 by an appropriate mechanism. A screw thread or even a fixed joint may be used. The embodiment illustrated includes a ball 18 and socket 19 arrangement (see FIGS. 3 and 4 for detail of the socket). This arrangement is preferred as it allows one to orientate the recess 13 to follow the axis II—II, and it is simple to connect the stem 17 to the gel holder 11. This is not the case with other mechanisms such as screw threads.

The device 10 is manufactured by forming the gel holder 11 by a suitable method such as injection moulding. Producing the holders 11 with inclined prongs 15 can be difficult using moulding methods. If angled pins are required, they could alternatively initially be moulded projecting perpendicularly to the recess base 14, and then subjected to heat, preferably in the form of a hot air flow. It has been found that a pair of inclined hot-air guns can be used to effect this quite satisfactorily. The airflow causes the prongs 15 to soften slightly and deform to an inclined angle. With adjustable airflow, adjustable power, adjustable height and adjustable speed of the conveyer passing the holders 11 under the air flow, the required angle of inclination can be obtained.

It has been found that passing the holders 11 on a conveyor under a pair of hot air guns at a speed of approximately 10 m/min with the air at a temperature of 410° C. works satisfactorily. The diameter of the air guns used for holders having a diameter of 54 mm in this working embodiment has been 50 mm. The air guns have been positioned adjacent each other in the machine direction, slightly offset with respect to each other and the holders 11 in the transverse direction to ensure that the entire surface of the holders 11 is covered by the air flow. The guns do not need to be angled with respect to the holders 11 and so the air flow is perpendicular to the holders 11. The holders 11 are then cooled in ambient temperature.

Once the holders 11 are formed, the recess 13 are filled with the gel in liquid form, and the gel allowed to set. The device 10 can then be packaged with or without the hanging means 12.

Although the air freshening device 10 is designed for use in a vehicle, it may obviously be used in any location where a suspended device is preferred. Alternatively, especially if used in a stationary environment, it can simply be placed (without the hanging means 12 if preferred) on a surface which is flat.

The device 10 may also be used for purifying the air by filling the holder 11 with a gel insecticide or other suitable composition.

The invention claimed is:

1. A device for an air freshener or purifier comprising a gel holder having at least one recess with a base for receiving a gel composition, wherein a plurality of prongs project from the base of the recess, with at least a majority of said prongs being inclined relative to an axis substantially perpendicular to the recess base in which the prongs are inclined in at least four different directions to said perpendicular axis.

2. A device according to claim 1 in which at least a majority of the prongs are arranged in rows, and the angle of inclination of the prongs in at least one row being towards the east, in at least another row to the west, in at least another row to the north and in at least another row south.

3. A device according to claim 1 in which the prongs are either straight or tapered.

4. A device according to claim 1 in which the angle of inclination lies in the range of 4° to 50°.

5. A device as claimed in claim 4 in which the angle of inclination is 8°.

6. A device according to claim 1 in which at least a majority of the prongs are provided in a plurality of straight rows.

7. A device as claimed in claim 6 in which the rows of prongs are provided in a plurality of groups.

8. A device according to claim 1 which further comprises hanging means for suspending the device.

9. A device as claimed in claim 8 in which the hanging means is removably or permanently attached to the gel holder.

10. A device according to claim 1 in which the gel holder is of a transparent material.

11. A device according to claim 1 in which the gel holder is of a plastics material.

12. A device according to claim 1 in which the number of prongs lies in the range of 10 to 100.

13. A device according to claim 1 in which the length of the prongs lies in the range of 1 mm to 10 mm.

14. A device according to claim 1 incorporating a gel composition.

15. A device as claimed in claim 14 in which the gel is a fragrance or air purifying composition.

16. A device as claimed in claim 14 in which the gel is an insecticide.

* * * * *